US009448180B2

(12) United States Patent
O'Dell et al.

(10) Patent No.: US 9,448,180 B2
(45) Date of Patent: Sep. 20, 2016

(54) MULTI-ANALYTE DETECTION SYSTEM AND METHOD

(75) Inventors: Brian Dwayne O'Dell, Stillwater, OK (US); Marcus LaGrone, Oklahoma City, OK (US); Martin Leuschen, Madison, WI (US)

(73) Assignee: FLIR Detection, Inc., Stillwater, OK (US)

( * ) Notice: Subject to any disclaimer, the term of this patent is extended or adjusted under 35 U.S.C. 154(b) by 717 days.

(21) Appl. No.: 13/516,088

(22) PCT Filed: Dec. 14, 2010

(86) PCT No.: PCT/US2010/060321
§ 371 (c)(1),
(2), (4) Date: Aug. 22, 2012

(87) PCT Pub. No.: WO2011/112222
PCT Pub. Date: Sep. 15, 2011

(65) Prior Publication Data
US 2012/0304729 A1    Dec. 6, 2012

Related U.S. Application Data

(60) Provisional application No. 61/286,529, filed on Dec. 15, 2009.

(51) Int. Cl.
| | |
|---|---|
| *C12M 1/34* | (2006.01) |
| *G01N 21/77* | (2006.01) |
| *G01N 33/00* | (2006.01) |
| *G01N 21/78* | (2006.01) |

(52) U.S. Cl.
CPC .......... *G01N 21/77* (2013.01); *G01N 33/0057* (2013.01); *G01N 21/783* (2013.01); *G01N 2021/7763* (2013.01); *G01N 2021/7786* (2013.01); *G01N 2021/7793* (2013.01); *G01N 2201/024* (2013.01)

(58) Field of Classification Search
CPC ........ G01N 33/48764; G01N 31/223–31/224; G01N 2021/8585; G01N 1/2273; G01N 2201/0214; G01N 2035/00019
See application file for complete search history.

(56) References Cited

U.S. PATENT DOCUMENTS

| | | | |
|---|---|---|---|
| 2,551,281 A * | 5/1951 | Moses et al. | 422/91 |
| 4,032,297 A * | 6/1977 | Lyshkow | 422/91 |
| 4,073,621 A | 2/1978 | Bull et al. | |
| 4,181,699 A | 1/1980 | Kitzinger | |
| 4,420,567 A | 12/1983 | McMahon et al. | |
| 4,806,491 A * | 2/1989 | Heim | 436/165 |

(Continued)

OTHER PUBLICATIONS

Restek Corporation, Brochure entitled Sulfinert Coatings for Sampling, Transfer, and Analysis of Sulfur Compounds to less than 20ppb, 2002.

(Continued)

*Primary Examiner* — William H Beisner
(74) *Attorney, Agent, or Firm* — Haynes and Boone, LLP (57) ABSTRACT

The invention provides for a multiple analyte detector that is capable of detecting and identifying explosive, chemical or biological substances having multiple analytes with a single system having multiple reporters. The reporters include fluorescent polymers, conducting polymers, metal oxide elements electrochemical cells, etc. The reporters may be combinations of other reporters that are optimized for broadband detection.

35 Claims, 8 Drawing Sheets

(56) References Cited

U.S. PATENT DOCUMENTS

| | | | |
|---|---|---|---|
| 5,077,010 A | * | 12/1991 | Ishizaka .................. B01L 3/505 422/408 |
| 5,397,536 A | | 3/1995 | Nakano et al. |
| 5,411,709 A | | 5/1995 | Furuki et al. |
| 5,491,097 A | | 2/1996 | Ribi et al. |
| 5,866,430 A | * | 2/1999 | Grow .............................. 506/6 |
| 5,928,609 A | | 7/1999 | Gibson et al. |
| 5,948,962 A | | 9/1999 | Matthiessen |
| 6,085,576 A | | 7/2000 | Sunshine et al. |
| 6,096,557 A | | 8/2000 | Tanaka et al. |
| 6,211,524 B1 | | 4/2001 | Vardeny et al. |
| 6,217,827 B1 | | 4/2001 | Zhang et al. |
| 6,230,545 B1 | | 5/2001 | Adolph et al. |
| 6,266,998 B1 | | 7/2001 | Hackenberg |
| 6,321,609 B1 | | 11/2001 | Mengel et al. |
| 6,635,415 B1 | | 10/2003 | Bollinger et al. |
| 6,649,403 B1 | | 11/2003 | McDevitt et al. |
| 6,649,416 B1 | | 11/2003 | Kauer et al. |
| 6,898,990 B2 | | 5/2005 | Rogers et al. |
| 6,985,818 B1 | | 1/2006 | Samuels |
| 7,005,292 B2 | | 2/2006 | Wilding et al. |
| 7,062,385 B2 | | 6/2006 | White et al. |
| 7,175,885 B2 | | 2/2007 | Lewis et al. |
| 7,189,353 B2 | | 3/2007 | Lewis et al. |
| 7,277,019 B2 | | 10/2007 | Povenmire |
| 7,295,308 B1 | | 11/2007 | Samuels |
| 7,359,802 B1 | | 4/2008 | Lewis et al. |
| 7,419,636 B2 | | 9/2008 | Aker et al. |
| 7,429,357 B2 | | 9/2008 | Truex et al. |
| 7,449,758 B2 | | 11/2008 | Axelrod et al. |
| 7,455,971 B2 | | 11/2008 | Chee et al. |
| 7,532,320 B2 | * | 5/2009 | Neiss et al. .................... 356/301 |
| 7,578,973 B2 | | 8/2009 | Call et al. |
| 2002/0188224 A1 | * | 12/2002 | Roe et al. ..................... 600/584 |
| 2004/0232052 A1 | | 11/2004 | Call et al. |
| 2007/0243618 A1 | | 10/2007 | Hatchett et al. |
| 2007/0295112 A1 | | 12/2007 | Swank et al. |
| 2008/0248578 A1 | | 10/2008 | Deans et al. |
| 2008/0311663 A1 | | 12/2008 | Bonne et al. |
| 2009/0030617 A1 | | 1/2009 | Schell et al. |
| 2009/0246883 A1 | | 10/2009 | McBrady et al. |

OTHER PUBLICATIONS

Aathithan, S. et al., Diagnosis of Bacteriuria by Detection of Volatile Organic Compounds in Urine Using an Automated Headspace Analyzer with Multiple Conducting Polymer Sensors, J. Clin. Microbiol., Jul. 2001, pp. 2590-2593.

Albert, Keith J. et al., Cross-Reactive Chemical Sensor Arrays, Chem. Rev. 2000, 100, pp. 2495-2626.

Bai, Hua et al., Gas Sensors Based on Conducting Polymers, Sensors 2007, 7, pp. 267-307.

Cunningham, Brian et al., A Plastic Colorimetric Resonant Optical Biosensor for Multiparallel Detection of Label-Free Biochemical Interactions, Sensors and Actuators B 85 (2002) pp. 219-226.

Dandin, Marc et al., Optical Filtering Technologies for Integrated Fluorescence Sensors, Lab Chip, 2007, 7, pp. 955-977.

de Silva, A. Prasanna et al., Sigaling Recognition Events wit Fluorescent Sensors and Switches, Chem. Rev. 1997, 97, pp. 1515-1566.

Hatfield, J.V. et al., Sensors and Actuators 8, 18-19 (1994) pp. 221-228.

Hierlemann, Andreas et al, Higher-Order Chemical Sensing, Chem. Rev. 2008, 108, pp. 563-613.

Lange, Ulrich et al., Conducting Polymers in Chemical Sensors and Arrays, Analytica Chimica Acta 614 (2008), pp. 1-26.

Liao, Frank et al., Organic TFTs as Gas Sensors for Electronic Nose Applications, Sensors and Actuators B 107 (2005), pp. 849-855.

Meany, Melissa S. et al., Luminescence-Based Methods for Sensing and Detection of Explosives, Anal Bioanal Chem (2008) 391:2557-2576.

Riken Keiki Co., Ltd., Development of a Monitoring Tape for Nitrogen Dioxide in Air, Analytica Chimica Acta 321 (1996) pp. 41-45.

Rock, Frank et al., Electronic Nose: Current Status and Future Trends, Chem. Rev. 2008, 108, pp. 705-825.

Thomas, Samuel W., III et al., Chemical Sensors Based on Amplifying Fluorescent Conjugated Polymers, Chem. Rev. 2007, 107, pp. 1339-1386.

White, Joel et al., Solid-State, Dye-Labeled DNA Detects Volatile Compounds in the Vapor Phase, PLos Biol. 2008, 12 pages.

* cited by examiner

MULTI-ANALYTE DETECTION SYSTEM AND METHOD

CROSS REFERENCE TO RELATED APPLICATIONS

Not Applicable.

STATEMENT AS TO FEDERALLY SPONSORED RESEARCH

Not Applicable.

BACKGROUND

Currently available gas-based detectors for explosives, hazardous chemicals, dangerous biological substances, or chemical/biological warfare substances have limited ability to detect multiple threats. For example, a single-target detector may be limited to one type of a particular reporter designed to respond to an analyte for a specific substance, such as a particular explosive or chemical. These detectors commonly have a short and limited operational period prior to replacement or servicing. Because a gas, such as an air sample, can carry more than one analyte from an explosive, a hazardous chemical, or a dangerous biological substance, multiple detectors are required for every use.

Government agencies involved in the inspection of transitory goods and/or people are usually responsible for the detection of explosives, hazardous chemicals or dangerous biological substances, or other contraband. These government agencies are looking for potentially masked or hidden dangerous substances that present a danger to the public. Using several different detectors with different reporters imposes a large logistical footprint and considerable consumable expense upon the governmental agencies. In practice, budgetary constraints force the governmental agency to purchase one or two detectors, each having a single reporter. Even if the governmental agency has several different detectors with different reporters, they may use only one detector to speed up the processing time of the transitory goods or people. The deployment of one type of detector over another means the agency is guessing as to which dangerous substance or other contraband they may encounter.

Unfortunately, anyone who observes the governmental agencies, or knows how the government typically operates, is able to ascertain the governmental agencies' practices and actions. This increases the threat from those intentionally creating these dangerous substances for nefarious reasons. The same dangerous situation occurs with those who ignorantly ship dangerous or hazardous substances. In both instances, limited deployment of multiple types of detectors increases the threat to harm to people and property.

Non-governmental agencies (NGA) also require systems capable of detecting and monitoring hazardous chemicals and biological substances quickly enough to prevent an accident. Similar to the government agency approach, the larger number of detectors required by the NGA increases the logistical footprint and associated expenses. When the NGA employs a single detector, they decide the most probable hazardous chemical or biological substance they will encounter. Unfortunately, chemicals and biological substances can change their properties when they are mixed, or when they contact other substances. To protect against the range of different types hazards requires several different types of detectors.

Of the known detectors, most use a porous membrane coated with a chemical or reporter. The selected reporters will respond to analytes carried by a gas. A sample interacts with the reporter, creating a specific response, such as fluorescing or undergoing a color change. The detection occurs as the sample flows through the porous membrane.

A detector and system is needed that can detect more than one explosive, chemical, biological substance and/or a combination thereof. Additionally, such a system needs to be lightweight, easily deployed, and reduce the consumable expenses by reducing the number of consumable elements. The easily portable multi-analyte detection system needs to minimize the impact of untargeted contaminates, as well as, decreasing the complexity for the end user, and decreasing the intervals between trade-outs of the consumable. Rapid detection of these substances saves lives and property.

SUMMARY

In one embodiment, the current invention provides an apparatus for detecting an analyte substance in a gas sample. The apparatus comprises a flow system carrying a sensor head and a heating block. The sensor head and the heating block define a module receiver therebetween. The apparatus has a gas inlet positioned on the sensor head and provides gaseous fluid communication to a sample area. The apparatus has a gas outlet positioned on the sensor head, and provides gaseous fluid communication from the sample area. The apparatus has a sealing edge positioned on the bottom of the sensor head and within the module receiver. The apparatus also has a heater positioned within the module receiver and positioned to provide heat to the sensor head, the heating block, and the module receiver. A module carrying a substrate is positioned within the module receiver, wherein the module carries a window. The substrate carries at least one reporter thereon. The reporter is selected for its ability to respond to a particular analyte carried by the gas sample. The substrate is exposed to the gas sample in the window of the module. The bottom of the sensor head, the sealing edge, and the substrate defines the sample area. The sealing edge and the substrate define a leak-free seal therebetween. The sample area is positioned within the window. The apparatus has at least one optical port in optical communication with the sample area. The optical port provides optical communication for at least one optical illuminator suitable for illuminating the sample area, and for at least one optical detector suitable for detecting a change in fluorescence, color, or a chemiluminescent reaction. The apparatus has a control system that is in electronic communication with the optical illuminator, the optical detector, and the module.

In another embodiment, a method for detecting multiple analytes is disclosed. The method comprises:
 a. capturing a gaseous sample with a detector, said detector carrying a sample port for receiving said gaseous sample and an exhaust port for expelling said gaseous sample;
 b. communicating said gaseous sample to a plurality of reporters, said reporters positioned upon a substrate carried by a removable module positioned within said detector;
 c. creating a response between an analyte and at least one said reporter, said analyte carried by said gaseous sample;
 d. detecting said response with a detector, said detecting step identifying said analyte;

e. notifying a control device regarding the identity of said analyte; and f. communicating said reporting step to a display, said communicating being controlled by said control device.

In still another embodiment, the current invention provides an apparatus for detecting an analyte substance in a gas sample. The apparatus comprises a detector, a module and a control system. The detector has a flow system and the flow system carries a sensor head and a heating block. The sensor head and the heating block define a module receiver therebetween. The sensor head has a sealing edge positioned thereon. The detector also has a gas inlet positioned on the sensor head, and provides gaseous fluid communication to a sample area. The detector has a gas outlet positioned on the sensor head and provides gaseous fluid communication from the sample area. The detector has a heater positioned within the module receiver and positioned to provide heat thereto. The detector has at least one optical port in optical communication with the sample area, wherein the optical port provides communication from an optical illuminator and an optical detector. The module houses a substrate, wherein the substrate carries a plurality of reporters thereon. The control system provides control of the detector, optical illuminator, optical detector, and module.

BRIEF DESCRIPTION OF THE DRAWINGS

FIG. 10 is a schematic perspective view of a flow system with a cartridge.

DETAILED DESCRIPTION

Figure 1A:
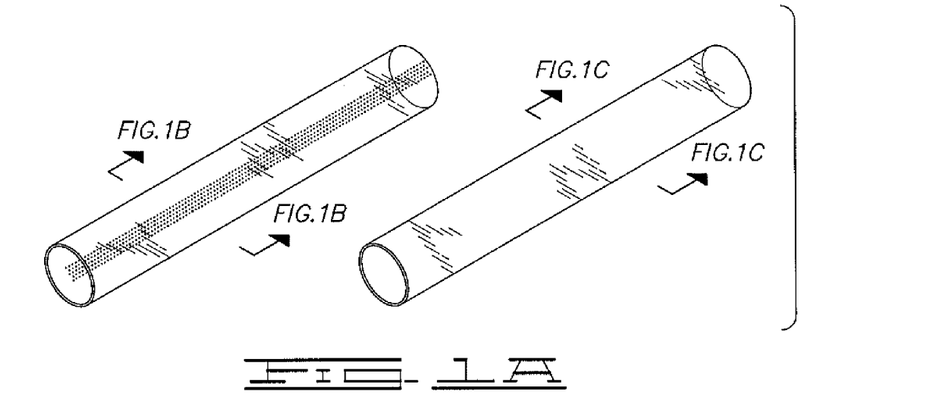
FIG. 1A is a schematic perspective view of prior art reporter vessels.
Figure 1B:
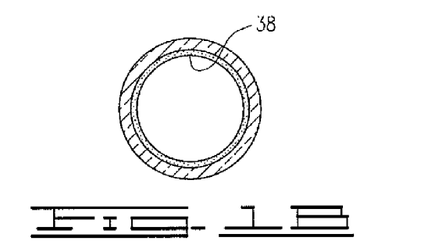
FIGS. 1B and 1C are end-views of the prior art reporter vessels of FIG. 1A showing the vessel with and without the reporter.
Figure 1C:
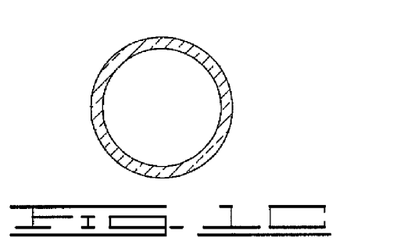
Figure 2:
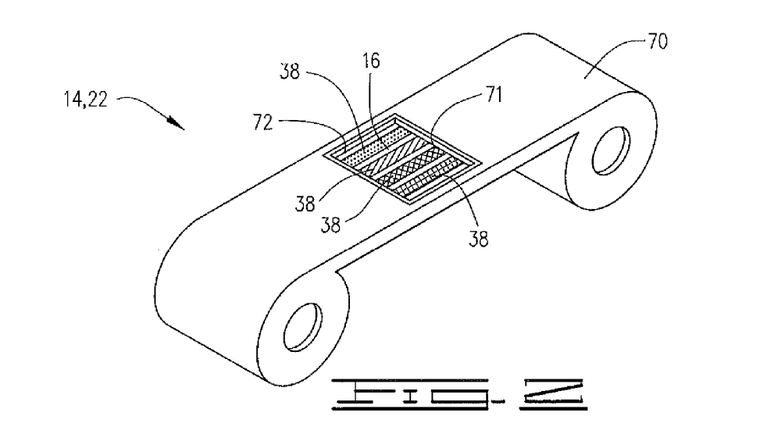
FIG. 2 is a schematic perspective view of a cartridge-based system of the current invention.

Referring to FIGS. 2-12B, the detection apparatus is illustrated and generally designated by the numeral 10. Detection apparatus 10 includes flow system 12, module 14, substrate 16 within module 14, detection system 18 and detector/processor system 20. Flow system 12 is capable of receiving module 14. Module 14 defines a storage and transport system for substrate 16. Module 14 can be in any shape, as discussed herein, and shown in FIGS. 2 and 6-9. For illustration purposes, module 14 is shown herein and generally referred to herein as cartridge 22. Cartridge 22 contains substrate 16 and exposes a portion of substrate 16 through window 72 to a gas flowing through flow system 12. FIG. 1 depicts rigid, fragile modules of the prior art.

Detection Apparatus

Figure 11:
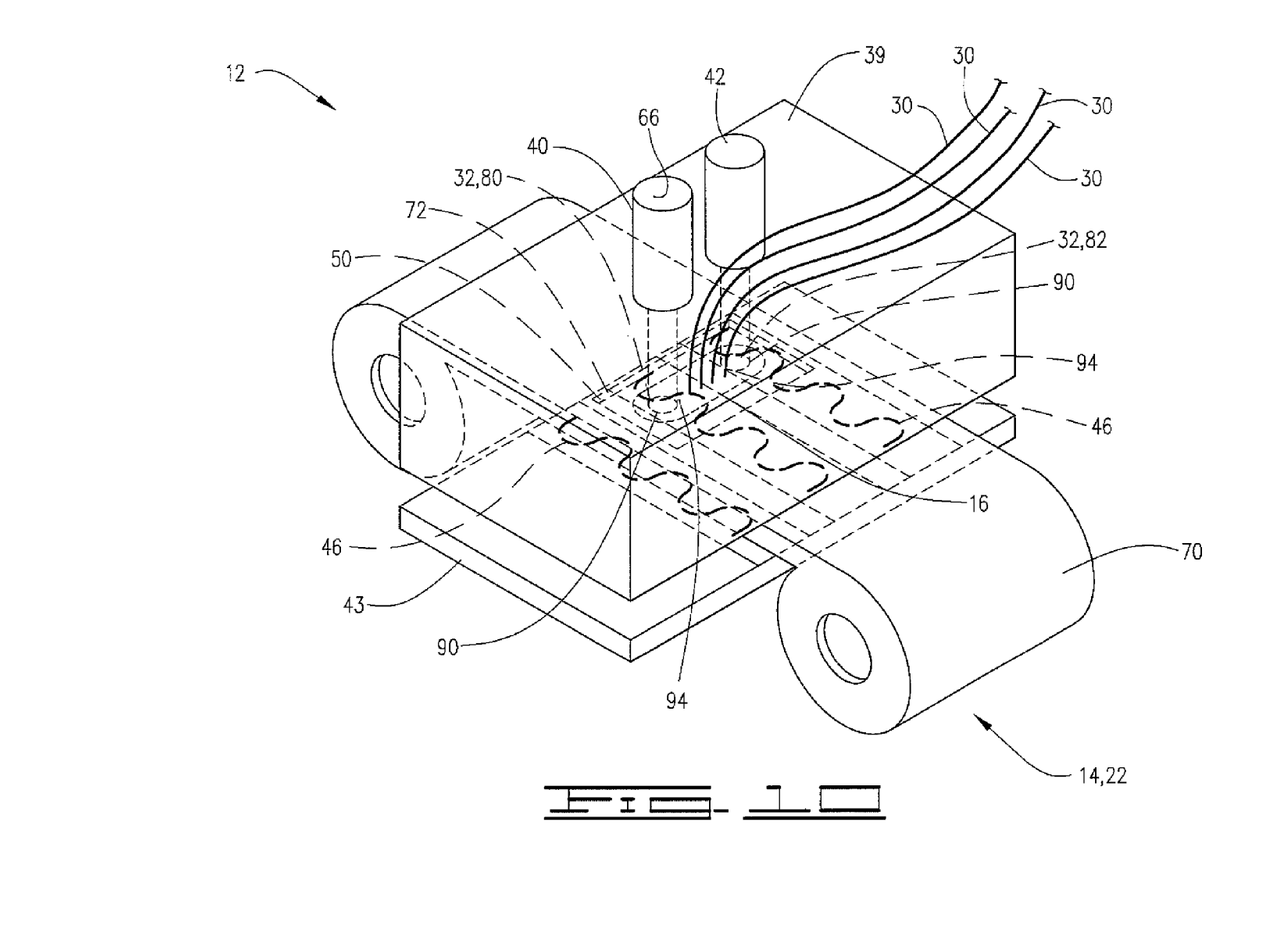
FIG. 11 is a schematic perspective view of a self-contained detection apparatus.
Figure 12A:
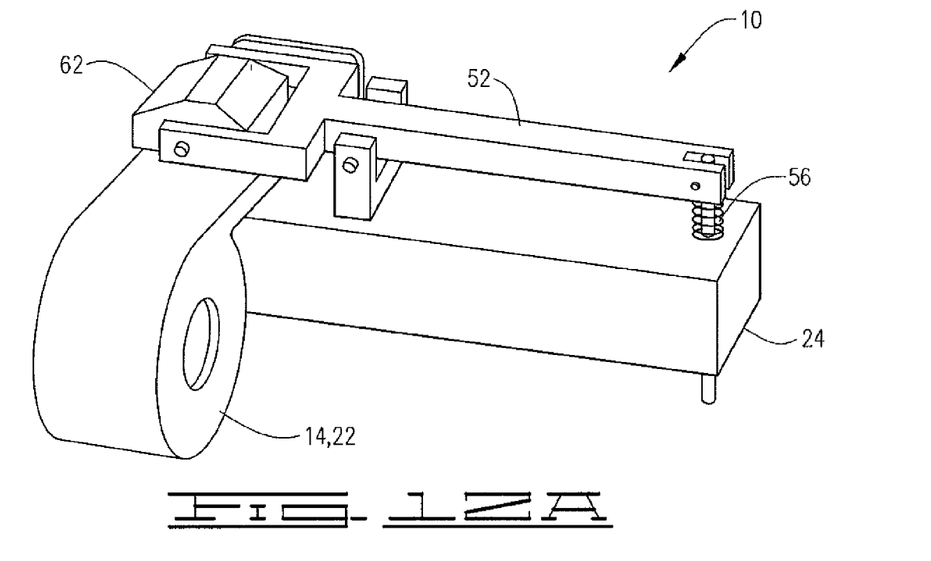
FIG. 12A is a schematic perspective view of a spring-biased lever arm self-contained detection apparatus.
Figure 12B:
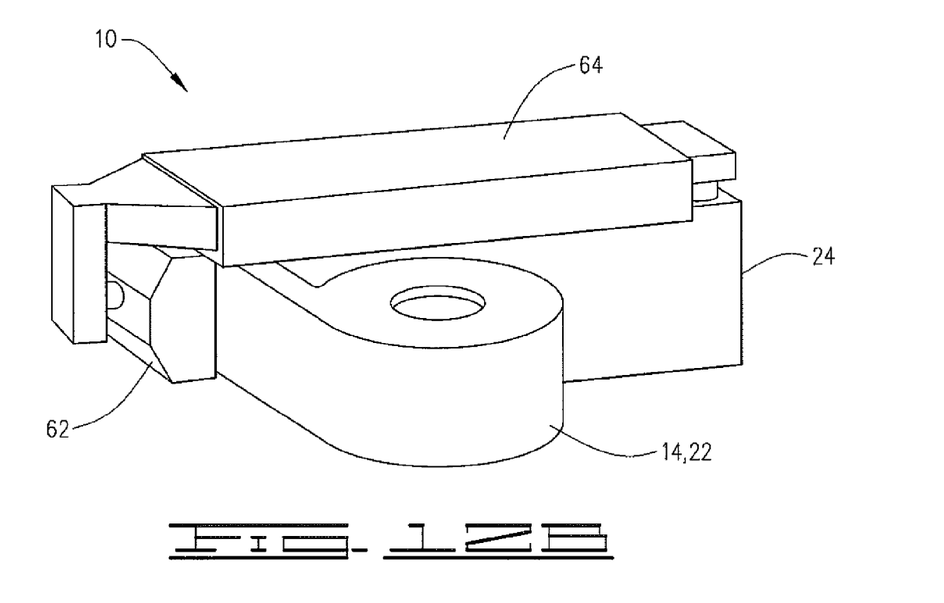
FIG. 12B is a schematic perspective view of a spring loaded slide self-contained detection apparatus.

In the preferred embodiment of FIGS. 10 and 11, detection apparatus 10 is positioned within housing 24. Detection apparatus 10 is also referred to as detector 10. FIGS. 12A and 12B, discussed below, are two alternative configurations of detection apparatus 10. To provide fluid communication between the external environment and flow system 12, housing 24 carries sample port 26 and exhaust port 28.

In a preferred embodiment, detection system 10 includes a plurality of fiber optic cables 30 connected to detection ports 32 of flow system 12. Fiber optic cables 30 provide optical communication with detection system 18. Preferably, housing 24 incorporates detection system 18 therein, as depicted in FIG. 11. Alternatively (not shown), housing 24 detachably connects to detection system 18.

Preferably, detection apparatus 10 includes power source 34, which provides power to all systems. Power source 34 is any convenient source of power, or sources of power, that provides sufficient power to the remainder of detection apparatus. Preferably, power source 34 includes a selectable plurality of sources of power.

Detection apparatus 10 also includes control system 36, which includes at least one processor, memory device, data entry port and communications port. Control system 36 provides the control of detection apparatus 10, which includes positioning substrate 16 within flow system 12, and detecting and processing the response when the analytes respond to reporters 38 as the gas sample passes over reporters 38. Commonly used reporters 38 are defined below. Preferably, control system 36 provides the processing capability to operate detection system 18 and the associated discrimination of the detected analyte. Control system 36 and detection system 18 are in electronic communication. Control system 36 preferably stores all electronic data and displays the pertinent information for an operator to take any necessary actions. The electronic storage device is preferably co-located with control system 36.

Regarding FIG. 12A, a different embodiment of detection apparatus 10 is shown where cartridge 22 is retained on housing 24 by spring-biased lever arm 52. Spring 56 provides the bias to spring-biased lever arm 52. In this embodiment, sensor head 39 is located within housing 24. In response to spring 56, sealing block 62 exerts pressure on cartridge 22, and provides for the sealing of substrate 16, cartridge 22 and sensor head 39.

Regarding FIG. 12B, another embodiment of detection apparatus 10 is shown where cartridge 22 is retained on housing 24 by spring-loaded slide 64. Similar to the embodiment shown in FIG. 12A, sensor head 39 is located in housing 24. Using a bias spring (not shown), spring-loaded slide 64 applies pressure to sealing block 62, which then exerts pressure on cartridge 22, and provides for the sealing of substrate 16, cartridge 22 and sensor head 39.

Flow System

Referring to FIGS. 4, 5, 10 and 11, housing 24 contains flow system 12 therein. Flow system 12 includes sensor head 39, gas sample inlet 40, gas sample outlet 42, heating block 43, at least one heater 46, bossed rim 48, and sample area 50. Heating block 43 and heater 46 cover an area at least as wide as substrate 16, and in some cases an area greater than that of substrate 16. The configuration of sensor head 39 and heating block 43 defines a module receiver 44. The defined module receiver 44 is configured to receive a module 14. Preferably, module 14 is selected prior to the design of flow system 12. As shown in FIGS. 10 and 11, module receiver 44 has a configuration suitable for permitting the insertion of window 72 of cartridge 22 between sensor head 39 and heating block 43 of flow system 12. In one embodiment, module receiver 44 operates to close around and seal module 14. FIGS. 12A and 12B depict two examples of this embodiment. However, those skilled in the art know the different types of closing and sealing mechanisms that will function with module receiver 44 as it closes about module 14, or cartridge 22. Window 72 provides access for the gas sample to interact with reporters 38 carried by substrate 16. Window 72 exposes the portion of substrate 16 and reporters 38 to flow system 12. Window 72 is open both above and below substrate 16, Gas sample inlet 40 provides gaseous fluid communication between sample port 26 and sample area 50. The bottom of sensor head 39, bossed rim 48, and substrate 16 define sample area 50. Bossed rim 48 provides a leak-free seal on substrate 16 for sample area 50. Sealing edge 49 includes bossed rim 48, as well as other known surfaces that provide a seal between the bottom of sensor head 39 and substrate 16. Thus, bossed rim 48 is a subset of sealing edge 49. Sample area 50 is positioned within window 72. Sample area 50 exposes reporters 38 on substrate 16 to a sample of gas communicated from sample port 26 across sample area 50. Gas sample outlet 42 communicates the gas sample from sample area 50 to exhaust port 28.

Pump 54, in gaseous fluid communication with exhaust port 28, creates a pressure drop between sample port 26 and exhaust port 28, thereby inducing flow across sample area 50. Although the preferred embodiment positions pump 54 internal to housing 24, the embodiment shown in FIG. 11 positions pump 54 externally. This demonstrates that pump 54 may be positioned anywhere between sample area 50 and exhaust port 28. Preferably, pump 54 creates a pressure drop sufficient to create a flow rate of about 1.0 liters/minute or less across sample area 50. In one embodiment, pump 54 selectively creates either a constant flow rate of at least 1.0 liters/minute or less, or a variable flow rate less than about 1.0 liters/minute. In another embodiment, pump 54 has only a constant flow of at least 1.0 liters/minute or less.

Figure 4:
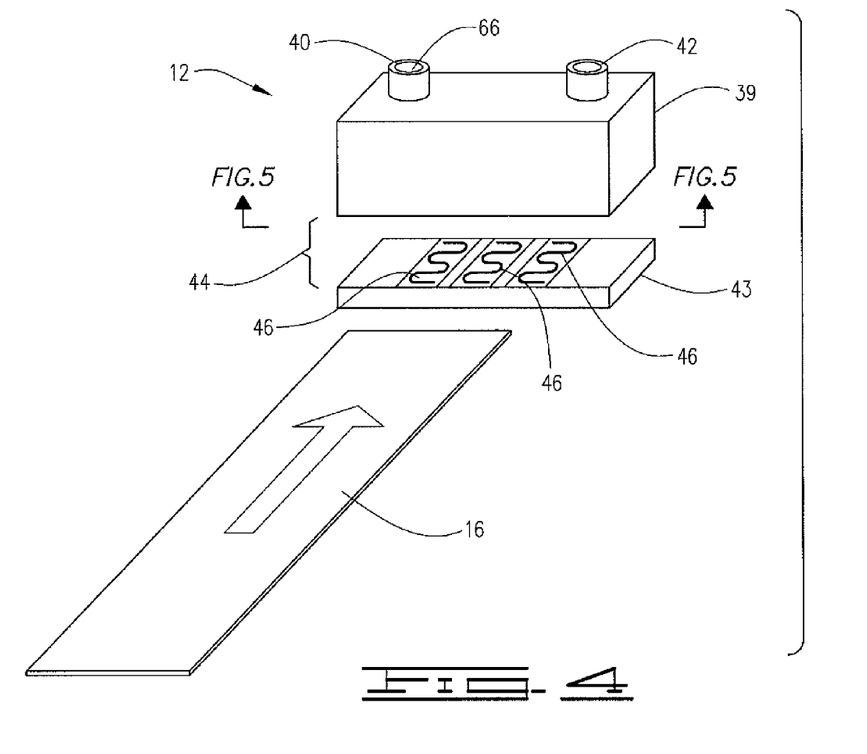
FIG. 4 is a schematic perspective view of a flow system for the detection apparatus.

Heater block 43 carries at least one heater 46. Preferably, heater 46 provides thermal input sufficient to increase the temperature of flow system 12 and substrate 16. By applying heat to flow system 12, the gas sample is more likely to convey the analytes from the external environment to sample area 50 and reporter 38. For example, a gas sample may contain trace amounts of an explosive matter. At room temperature, the trace amounts of explosive matter begin to adhere to the surface of intake 66. By heating flow system 12, the gas sample is less likely to adhere. Thus, the warmer flow system 12 keeps the trace amounts of explosive matter in a gaseous state and suspended within the gas sample. Preferably, heater 46 maintains heating flow system 12 at an operating temperature between about 40° C. and about 200° C. FIG. 4 depicts a non-limiting example of a placement of heater 46. Heater 46 may be placed anywhere on flow system 12 that provides sufficient heating. When heated, substrate 16 is also heated by heater 46, or alternatively, substrate 16 is heated by a separate source (not shown).

Module/Cartridge

Figure 6:
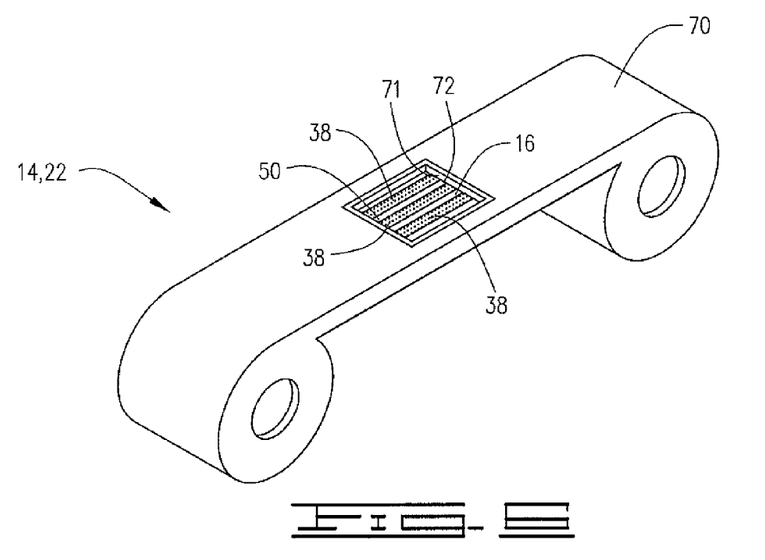
FIGS. 6-9 are schematic perspective views of different modules containing the substrate.
Figure 7:
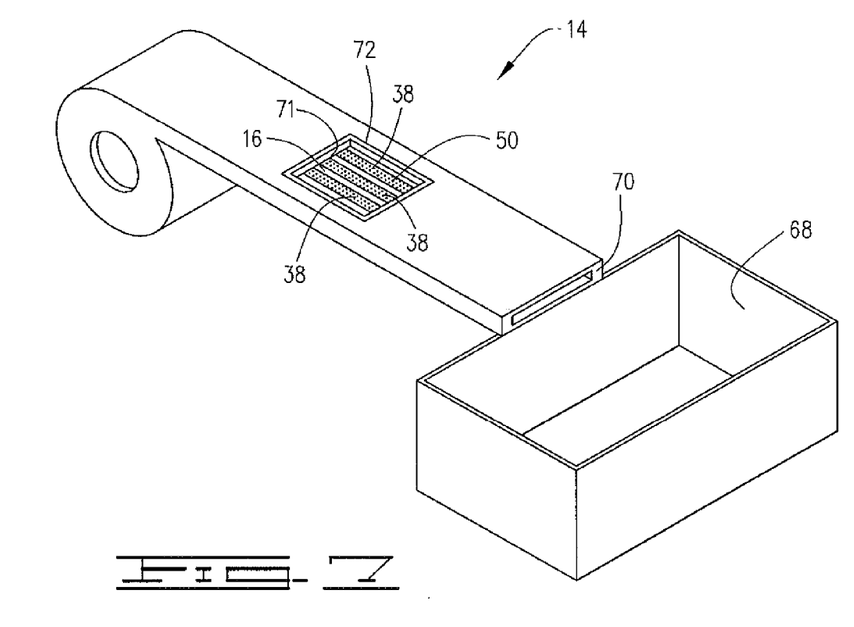
Figure 8:
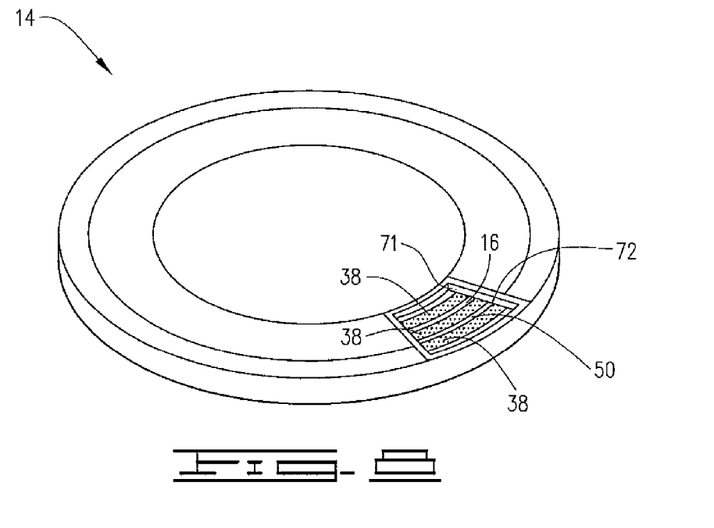
Figure 9:
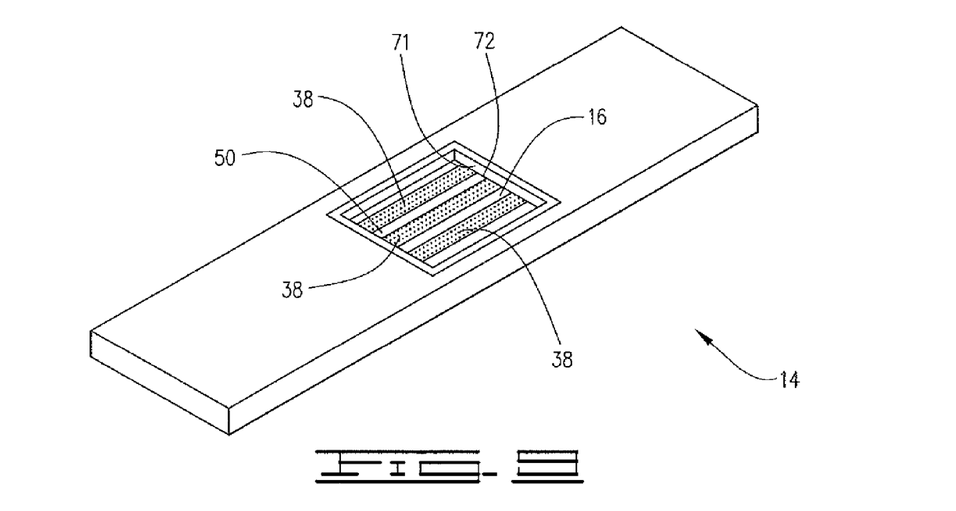

As previously indicated, cartridge 22 is used throughout to represent module 14. However, cartridge 22 represents only one possible, non-limiting configuration of module 14. The skilled artisan understands that module 14 may be in any shape capable of holding and conveying substrate 16 to sample area 50. FIGS. 6-9 depict four examples of module 14. FIG. 6 depicts cartridge 22 as module 14. FIG. 7 depicts a variation of a cartridge as module 14 having a single storage reel that feeds substrate 16 through window 72 and sample area 50 into catch bin 68. FIG. 8 depicts a disk-type version of module 14 for transporting substrate 16 through window 72 and sample area 50. FIG. 9 depicts a strip-like version of module 14 for providing transport of substrate 16 through window 72 and sample area 50. Any form of module 14 will work. However, in one embodiment, module 14 has a sealed storage capacity for substrate 16 and it provides for the movement of substrate 16 through window 72 and sample area 50. In another embodiment, module 14 has an unsealed storage capacity for substrate 16 and it provides for the movement of substrate 16 through window 72 and sample area 50.

To preclude false positives, contamination, and loss of reporter 38 material, module 14 includes seal 71 or other configuration that precludes premature exposure of substrate 16 to the environment. In one embodiment, unexposed substrate 16 is sealed within module 14 from premature exposure for any of the aforementioned module 14 examples. In one alternative embodiment using cartridge 22, end 70 of cartridge 22 is isolated by seal 71 at window 72 thereby precluding exposure of reporters 38 on substrate 16 housed within end 70. In this embodiment, seal 71 flexes sufficiently to permit advancement of substrate 16 to window 72 for exposure within sample area 50 without loss of reporter from substrate 16. Preferably, seal 71, when used, is a material that does not respond to any of the potential reporters 38 or substrate 16. Seal 71 may be made from a variety of materials such as felt, rubber, paper, silicone, neoprene, other non-responsive materials, and combinations thereof.

Continuing with the illustration of module 14 with cartridge 22, cartridge 22 has window 72 exposing substrate 16 to sample area 50. Preferably, the size of window 72 allows bossed rim 48 of module receiver 44 to fully contact substrate 16, such that the activation of pump 54 creates a vacuum sealing substrate 16 to bossed rim 48. Thus, bossed rim 48 or sealing edge 49, in cooperation with the top of substrate 16 and the bottom of sensor head 39, defines sample area 50. Thus, activation of pump 54 will pull the sample gas in through gas sample inlet 40 passing the sample over reporters 38 carried by substrate 16, and subsequently directing the gas sample out through gas sample outlet 42.

Cartridge 22 automatically advances substrate 16 through sample area 50 after a pre-determined period, or after a detection event. This automatic advancement optimizes the exposure of reporter 38. The advancing mechanism for cartridge 22 may be of any type known to those skilled in the relevant art. Some non-limiting examples include manual advance devices, electric or pneumatic motors, solenoids, pistons, or other electro-mechanical or electro-pneumatic device. Control of the associated advancement of cartridge 22 is accomplished using control system 36. Substrate 16 is advanced from the edge of the exposed area until an entirely new, unexposed area of substrate 16 is within window 72. For the non-sealed embodiment of cartridge 22, substrate 16 advances and reporter 38 remains unaffected. For the sealed embodiment of cartridge 22, a sealing element (not shown) allows substrate 16 and reporter 38 to advance without damaging reporter 38. In one embodiment, substrate 16 may carry a removable protective layer (not shown) to protect reporter(s) 38 in cartridge 22. The removable protective layer is automatically removed as substrate 16 advances into window 72.

Preferably, identification of cartridge 22 to control system 36 occurs during installation. A barcode, a radio frequency identification (RFID) chip, manually entered descriptive identifier, or any other identifier provides the unique identifier for cartridge 22 as it is installed. The unique identifier allows control system 36 to identify cartridge 22 and obtain data concerning reporters 38 supplied with the installed cartridge 22. The unique identifier associated with cartridge 22 facilitates the control, operation and distribution of cartridge 22.

Once cartridge 22 has been identified, control system 36 optimizes the exposure of substrate 16 based upon the indicated reporters 38, and the number of exposures, illuminations, and durations thereof. Automation and control for advancing of cartridges 22 is well known to those skilled in the art of cartridge making, and not detailed herein.

Substrate

Figure 3A:
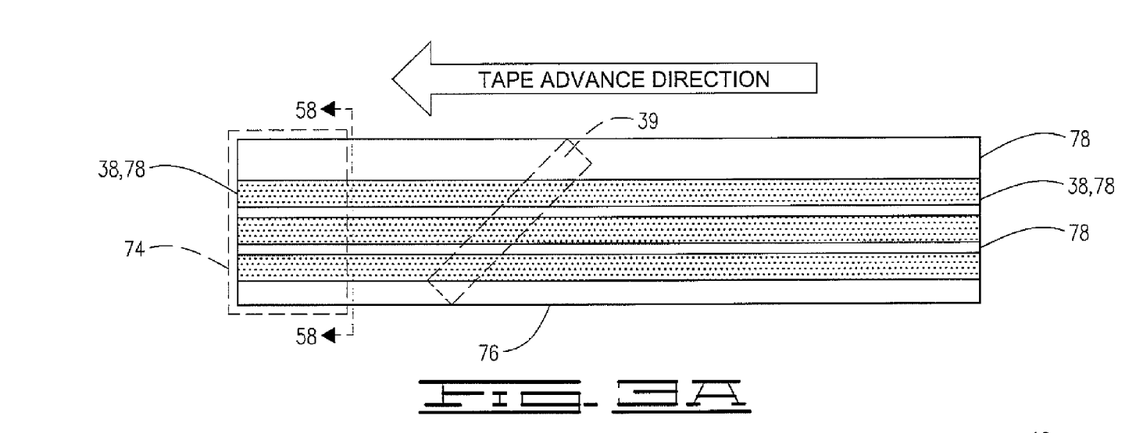
FIGS. 3A and 3B are schematic plan views of multiple reporter substrates.
Figure 3B:
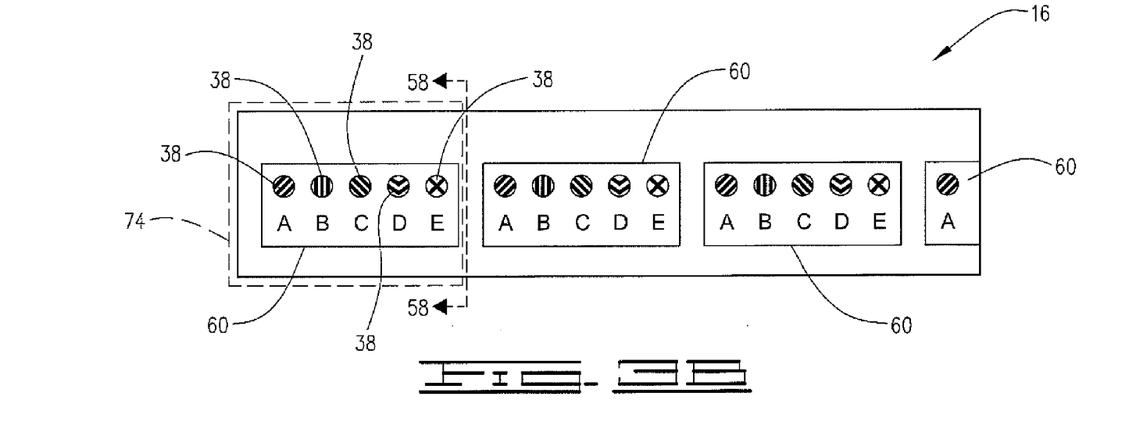

Substrate 16 is a nonporous medium suitable for carrying a variety of reporters 38. As a non-limiting example, FIG. 3A shows a preferred substrate 16 having reporter(s) 38, optional calibration strip 74, and/or optional preconditioning strips 76 positioned thereon. Preferably, reporter(s) 38 are adhered to substrate 16 and/or disposed on a definable segment of substrate 16 in tracks 78. FIG. 3A depicts an example of a substrate 16 carrying a plurality of reporters 38 and optional preconditioning strips 76. FIG. 3A also depicts using segment 58 of substrate 16 as calibration strips 74. FIG. 3B depicts an alternative embodiment of substrate 16 with reporter(s) 38 in sequential order in block segments 60.

Unlike the glass-based prior art examples of FIG. 1, when used in cartridge 22, substrate 16 is preferably a flexible material which retains its integrity up to a temperature of about 200° C. Alternatively, substrate 16 in module 14 is a rigid plate or disk as shown in FIG. 8. Substrate 16 may be opaque, translucent or transparent as long as it is consistent with the placement of optical illuminator(s) 84 and detection system 18 relative to substrate 16. Substrate 16 preferably is electrically non-conductive, but has sufficient thermal conductivity to allow heating of reporters 38.

Particularly preferred substrate 16 material will not respond to reporters 38. For example, substrate 16 may be a plastic selected from the group consisting of polyethylene terephthalate (PET), Polyethylene Terephthalate Glycol (PETG), polyethylene naphthalate, cyclo-olefin copolymer, polycarbonate, polyimide, cellulose acetate, cellulose triacetate, acrylics, styrenes, and combinations thereof Additionally, the aforementioned plastics may be hard coated. As known to those skilled in the art, these compounds may be processed and formulated to provide the flexibility necessary for use in cartridge 22.

Preferably, substrate 16 must be able to perform the function of a gasket for the bossed rim 48. To ensure adequate flow through sample area 50, substrate 16 may not be porous nor allow any flow of the gas sample therethrough. Substrate 16 must be able to seal against bossed rim 48 when pump 54 creates a pressure drop across sample area 50. The seal between substrate 16 and bossed rim 48 prevents unwanted leakage into sample area 50 or contamination of the gas sample. However, substrate 16 must have sufficient roughness to allow reporters 38 to adhere thereto. Optionally, a non-reactive, non-responsive o-ring (not shown) assists in the sealing of bossed rim 48 to substrate 16. Alternatively, a combination of a rigid surface, a rimmed surface, a compliant surface, or an o-ring assists in the sealing of bossed rim 48 to substrate 16.

Optional calibration strip 74 provides a known reporter-type response to detection system 18 during initial insertion of cartridge 22 into flow system 12. For example, if reporter 38 is a fluorescing type of reporter, optional calibration strip 74 will provide a known response for checking the operation of the components of detection apparatus 10. Optional calibration strip 74 provides a signal to detection apparatus 10 to verify strength of the signal and quality of the signal.

Optional preconditioning strips 76 positioned on substrate 16 upstream of the gas sample flow provide a binding agent to capture contaminates. Preferably, optional preconditioning strips 76 capture contaminates. Optional preconditioning strips 76 are preferably positioned on block segment 60 of cartridge 22 near gas sample inlet 40.

Detection System

The response between an analyte in the gas sample and reporter 38 may produce a fluorescent response, may produce a change in the fluorescence, a change in color, or a change in the chemiluminescence. Detection system 18 detects responses to an analyte exposed to the portion of substrate 16 carrying reporter 38. The response optically transmits from sample area 50 to detector/processor system 20. Detector/processor system 20 provides analysis and positive identification of an analyte of the gas sample. Detector/processor system 20 communicates the analysis and identification of the analyte to control system 36. Control system 36 provides for the tracking of gas sample history and visual identification. However, those skilled in the relevant art understand that detector/processor system 20 is capable of providing these same functions.

Figure 5:
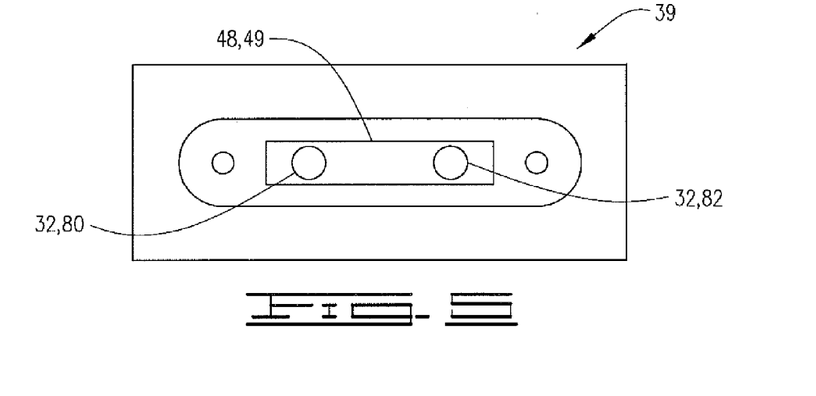
FIG. 5 is a schematic bottom view of a flow system.

Preferably, detection system 18 shown in FIG. 4, detects the response of the analyte in module receiver 44 at optical port 80 and/or optical port 82. In the preferred embodiment, optical ports 80 and 82 are utilized. As shown in FIGS. 5 and 10, optical ports 80 and 82 are below substrate 16. Optical ports 80 and 82 may be positioned above, below or anywhere in an optical line of sight, or can be optically conducted to substrate 16, as long as optical illuminator 84 and optical detector 86 are able to optically communicate with substrate 16 and reporter 38 within sample area 50 while a response is occurring between the gas sample and reporter 38.

Detection system 18 has at least one optical illuminator 84 and at least one optical detector 86. Optical illuminator 84 and optical detector 86 are positioned to be in direct or indirect optical communication with either optical port 80 or optical port 82. Preferably, optical illuminator 84 and optical detector 86 have fiber optic cables 30 providing the optical communication between optical ports 80 and 82 and optical illuminator 84 and optical detector 86.

As shown in FIG. 11, optical illuminator 84 is positioned within illuminating system 81, and optical detector 86 is positioned within detector/processor system 20 where they transmit and receive an optical signal via fiber optical cable 30. It is understood that optical illuminator 84 and optical detector 86 may be positioned anywhere they are able to transmit and/or receive the optical signal. Other optical relay methods may be used, by way of a non-limiting example: light pipes, imaging and non-imaging relay optics, close proximity coupling of detector 86 with substrate 16, or combinations thereof.

In the preferred embodiment, fiber optical cable 30 has a first end 90 and a second end 92 to provide illumination. First end 90 is disposed in optical port 80 and/or optical port 82. Second end 92 is connected to optical illuminator 84 within illumination system 81. An example of an optical illuminator 84 is a light-emitting diode (LED) having a specific wavelength. As stated, optical port 80 and/or optical port 82 may be positioned above or below substrate 16. Power for illumination system 81 can be the aforementioned sources of electrical identified for power source 34.

Optical illuminator 84 is preferably capable of generating light in the ultraviolet range to create fluorescing in reporter 38. Preferably, a plurality of optical illuminators 84 are used to generate a plurality of illuminations. Each of the plurality of illuminations is preferably in a wavelength that is different from each of the other illuminations. In operation, the plurality of illuminators 84 sequentially interrogate reporters 38 to prevent cross-contamination of an optical signal. However, optional programming of optical illuminators 84 provides for the interrogation of reporters 38 in any order. The desired response from reporter 38 determines the order of interrogation. The programmed interrogation of reporters 38 includes the ability to interrogate them simultaneously.

In one embodiment, a plurality of optical illuminators 84, each having a different wavelength, are used to increase the breadth of coverage by using more reporters 38, thereby increasing the opportunity for detection of a plurality of different analytes. In another embodiment, a plurality of optical detectors 86 are used to increase the opportunity to capture a detection signal, thereby providing for a greater opportunity to verify the identity of the sample substance under scrutiny. In yet another embodiment, a plurality of both optical illuminators 84 and optical detectors 86 are used.

In the preferred embodiment, a second fiber optic cable 30 having first and second ends 94 and 96, provides optical communication between either of optical ports 80 and 82 for optical detector 86. First end 94 is in optical communication with either of optical ports 80 and 82. Second end 96 is in optical communication with optical detector 86. The second fiber optic 30 is not used for illumination purposes, but may be co-located with the first fiber optic cable 30 in either of optical ports 80 and 82 while the first fiber optic cable is used for illumination purposes. Optical detector 86 is capable of converting the optical signal to an electrical signal. Optical detector 86 is positioned within the detector/processor system 20. Power for optical detector 86 is the aforementioned power source 34.

Preferably, sensor head 39 is positioned to maximize the efficiency of detection system 18. As shown in FIG. 3A, sensor head 39 of detection system 18 is angled relative to substrate 16. The angling increases the surface area of reporter 38 during interrogation. However, sensor head 39 can be also be orthogonal or parallel to reporter(s) 38.

Reporters

In a preferred embodiment, detection apparatus 10 simultaneously utilizes numerous reporters 38 on substrate 16 in multiple tracks. Furthermore, each track may include a plurality of reporters 38. Additionally, detection apparatus 10 may optionally include multiple bright field reporters 38 and multiple dark field reporters 38.

Bright field reporters 38 require active illumination. The response to an analyte produces a detectable change in fluorescence or color. Dark field reporters 38 are commonly chemiluminescent and do not require active illumination. These reporters produce light in response to a target analyte. Dark field reporters 38 do not have any control mechanism turning them on or off. Preferably, when module 14 includes more than one dark field reporter, the dark field reporters will be separated into zones based on the known wavelength of the resulting light.

Reporters 38 will vary based upon need, but a representative example includes Amplifying Fluorescence Polymers (AFPs), other fluorescent materials, Chemical Warfare Indicating Chromophore (CWIC), other chemiluminescent materials, Phenyl Quinoline (PQ), polymers, colorimetric materials, organic thin film transistors, metal, metal-oxide based sensors, or a combination thereof As other reporters 38, or more refined reporters 38, are developed, they will become candidates for use on substrate 16. Some reporters 38 are single exposure, but most commonly known reporters 38 are capable of receiving multi-exposures before losing their responsiveness.

As stated before, reporters 38 are preferably adhered to substrate 16. Some methods for depositing reporters 38 to substrate 16 may include ink-jet application, direct deposit, lithography, screen printing, vacuum sealing, heating, laminating, or some other method that provides for the application of multiple reporters 38 on the same substrate 16 and prevents cross-contamination of reporters 38. Reporters 38 will usually have a thickness in the range of about 0.5 microns to about 0.5 millimeters.

Environmental

In one embodiment, detection apparatus 10 must be able to operate in closed environments around humans who are not wearing any special protective gear. In another embodiment, detection apparatus 10 must withstand combat deployment conditions such as found in desert, tropical, temperate and cold climates. Additionally, detection apparatus 10 is preferably able to withstand shipping and handling by untrained personnel. Thus, detection apparatus 10 is preferably able to withstand a fall from about a three (3) foot height without adding any additional protection measures. In addition, detection apparatus must withstand repeated bouncing in a closed container.

Operational Considerations/Impacts

Preferably, detection apparatus 10 employs different modules 14 for different threats. For example, if a detection apparatus is using cartridges 22, and if there is a threat of an explosive compound or biological substance, the operator selects the cartridge that can detect either of these threats. Alternatively, if the threats relate to chemical warfare agents and explosive compounds, the operator selects a cartridge 22 that is capable of detecting both these threats. However, it is understood, that cartridge 22 may have a series of reporters 38 for detecting a specific threat within a category such as explosives, chemical warfare agents, biological warfare agents, and/or hazardous chemicals.

Detection apparatus 10 is usable in the field by personnel having minimal training. Thus, replacing module 14 is preferably an easy task. When cartridge 22 reaches the end of the unexposed substrate 16, the field personnel are able to remove and insert a new cartridge 22. In one embodiment, the replacement interval of cartridge 22 is in excess of eight hours. In another embodiment, cartridge 22 (module 14) will have a replacement interval of about three to four weeks. Alternatively, the number of exposures or gas samples defines the replacement interval of cartridge 22.

The detectors of detection system 18 determine if contamination of reporter 38 and/or substrate 16 has occurred. For example, photo bleaching or oxidation potentially affects a reporter's effectiveness. The detectors periodically interrogate reporter 38 to identify the state of reporter 38. The detectors also monitor the degradation of the brightness of a response from reporter 38. If the detector finds a contaminated or degraded reporter 38, control system 36 advances substrate 16 within cartridge 22 to a new, unexposed segment.

When a detection event occurs, control system 36 generates a display (not shown) on detection apparatus 10 and/or an electronic signal for transmittal to another device. An audible signal may also be generated. The operator can take appropriate action based upon the type of substance detected in the gas sample.

After a detection event is over, pump 54 purges sample area 50 by passing a sufficient quantity of uncontaminated air across sample area 50. Control system 36 advances substrate 16 within cartridge 22, presenting a fresh set of reporters 38.

Method

A method of use of detection apparatus 10 includes placing it where sample port 26 captures and receives a gas sample carrying at least one analyte. Due to the pressure drop created by pump 54, the gas sample is communicated from sample port 26 to gas sample inlet 40, across sample area 50 and reporters 38, through gas sample outlet 42 and is expelled through exhaust port 28. The analyte responds to at least one reporter 38 positioned on substrate 16.

In one embodiment, the analyte responds to a bright field reporter 38. The method includes actively illuminating the bright field reporter 38 with optical illuminator 84. The active illuminating step occurs within sample area 50. A non-limiting example uses an ultraviolet LED illuminator 84 that propagates light from illuminating system 81 across the first fiber optic cable 30 to sample area 50, thereby causing the analyte to fluoresce. Upon response of reporter 38 to the analyte, optical detector 86, in detector/processor system 20, detects the change in fluorescence of reporter 38 in response to the analyte. The second fiber optic cable 30 optically communicates the detected change in fluorescence from sample area 50 to optical detector 86.

In another embodiment, the analyte responds to a dark field reporter 38. Since the dark field reporter 38 is chemiluminescent, optical detector 86 is continually monitoring reporter 38 for a response between reporter 38 and the analyte. In the event a response occurs, reporter 38 emits fluorescence within sample area 50. Fiber optic cable 30 optically communicates the fluorescence from sample area 50 to optical detector 86 in detection/processor system 20.

For both embodiments, detector/processor system 20 and optical detector 86 process the particular response. And, based upon the prior identification of module 14 and reporters 38 contained therein, notifies control system 36 of the identity of the particular analyte. Display of the resulting identification provides the operator immediate notification of the presence of an analyte in the gas sample. Control system 36 communicates the identity of analyte to the display. Control system 36 records all operations for future reference. Once the event is over, control system 36 communicates to the automated advancing system to advance substrate 16 to an unexposed section.

Control system 36 continually monitors module 14. When all, or substantially all, of substrate 16 is consumed, or mostly consumed, control system 36 notifies the operator of a need to replace module 14.

Other embodiments of the current invention will be apparent to those skilled in the art from a consideration of this specification or practice of the invention disclosed herein. Thus, the foregoing specification is considered merely exemplary of the current invention with the true scope thereof being defined by the following claims.

What is claimed is:

1. An apparatus for detecting an analyte substance in a gas sample, comprising:
    a flow system carrying a sensor head and a heating block, said sensor head and said heating block defining a module receiver therebetween;
    a gas inlet positioned on said sensor head and providing gaseous fluid communication to a sample area;
    a gas outlet positioned on said sensor head and providing gaseous fluid communication from said sample area;
    a sealing edge positioned on the bottom of said sensor head and within said module receiver;
    a heater positioned within said module receiver and positioned to provide heat to said sensor head, said heating block, and said module receiver;
    a removable module positioned in said module receiver and carrying a substrate and a substrate feeder capable of advancing said substrate through said module, said module carrying a window;
    said substrate carrying at least two different reporters thereon, wherein said two different reporters are selected for their ability to respond to at least one analyte carried by said gas sample, wherein said substrate is exposed to said gas sample in said window, wherein said sample area is defined by said bottom of said sensor head, said sealing edge, and said substrate, wherein said sealing edge and said substrate define a leak-free seal therebetween, and wherein said sample area is positioned within said window;
    wherein said sample area isolates a portion of said substrate carrying said at least two different reporters thereon from a remainder of said substrate located outside said sample area, and wherein said sample area precludes contamination of said remainder of said substrate located outside of said sample area;
    at least one optical port in optical communication with said sample area, said optical port providing optical communication for at least one optical illuminator and for at least one optical detector communicating therethrough; and
    a control system in electronic communication with said optical illuminator, said optical detector, and said module, said control system comprising a processor and a memory device.

2. The apparatus of claim 1, further comprising at least one preconditioning strip positioned on said substrate.

3. The apparatus of claim 1, wherein said at least two different reporters in said sample area includes a reporter for detecting explosives and a reporter for detecting hazardous chemicals.

4. The apparatus of claim 1, wherein said at least two different reporters in said sample area includes a reporter for detecting explosives, a reporter for detecting chemical warfare agents, and a reporter for detecting biological warfare agents.

5. The apparatus of claim 1, wherein said at least two different reporters in said sample area includes a reporter for detecting hazardous chemicals.

6. The apparatus of claim 1, wherein said at least two different reporters in said sample area includes a reporter for detecting explosives.

7. The apparatus of claim 1, wherein at least two different reporters in said sample area includes a reporter for detecting biological warfare agents.

8. The apparatus of claim 1, wherein said at least two different reporters in said sample area includes a reporter for detecting chemical warfare agents.

9. The apparatus of claim 1, further comprising a contaminate binder positioned near said gas inlet.

10. The apparatus of claim 1, wherein said module is removable and replaceable with a module carrying a different set of reporters.

11. The apparatus of claim 1, wherein said module is removable and replaceable with a new module.

12. The apparatus of claim 1, wherein said removable module is a reel-to-reel cartridge.

13. The apparatus of claim 1, wherein said removable module is a strip feed cartridge.

14. The apparatus of claim 1, wherein said removable module is a rotating disk cartridge.

15. The apparatus of claim 1, wherein said removable module has at least one reel containing a substantial portion of unexposed portions of said substrate prior to initial use of said module.

16. The apparatus of claim 1, wherein said substrate feeder is capable of automatically advancing said substrate in said module through said window, thereby exposing said substrate to said sample area.

17. The apparatus of claim 1, wherein said heater is positioned above or below said substrate within said module receiver.

18. The apparatus of claim 1, wherein said heater is configured to heat a gas inlet or a sample port of the apparatus to lessen the likelihood of said at least one analyte to adhere to said gas inlet or sample port.

19. The apparatus of claim 1, further comprising an identifier on said module, said identifier establishing the particular type of module carrying a specific reporter or set of reporters.

20. The apparatus of claim 1, further comprising a substrate seal providing protection against accidental premature exposure of said at least two different reporters.

21. The apparatus of claim 20, wherein said substrate seal is a gasket comprised of a material selected from the group consisting of felt, rubber, paper, silicone, neoprene, other non-responsive materials, and combinations thereof, wherein the substrate comprises a flexible substrate, and wherein the flow system is configured to draw the gas sample from the gas inlet through the sample area and the gas outlet and cause a pressure drop or vacuum helping to form the leak-free seal between the flexible substrate and the sealing edge.

22. The apparatus of claim 1, wherein said substrate is capable of withstanding temperatures up to 200° C.

23. The apparatus of claim 1, wherein said reporter is laminated on said substrate.

24. The apparatus of claim 1, further comprising a calibration strip, said calibration strip positioned on a first segment of said substrate, wherein said first segment defines the start of said substrate.

25. An apparatus for detecting an analyte substance in a gas sample, the apparatus comprising:
a detector, wherein the detector includes:
a flow system carrying a sensor head and a heating block, wherein the sensor head and heating block define a module receiver therebetween, and wherein the sensor head has a sealing edge positioned thereon;
a gas inlet providing gaseous fluid communication to a sample area;
a gas outlet providing gaseous fluid communication from the sample area;
a heater positioned within the module receiver and providing heat thereto;
at least one optical port in optical communication with the sample area, wherein the optical port provides communication from an optical illuminator and an optical detector;
a removable module housing a substrate, wherein the substrate carries a plurality of reporters thereon, said module including a substrate feeder capable of advancing said substrate through said module and into said sample area, wherein said sample area isolates a portion of said substrate carrying at least two different reporters thereon from a remainder of said substrate located outside said sample area, and wherein said sample area precludes contamination of said remainder of said substrate located outside of said sample area; and
a control system providing control of the detector, optical illuminator, optical detector, and module, said control system comprising a processor and a memory device.

26. A method of detecting multiple analytes using the apparatus of claim 25, the method comprising:
capturing said gas sample with said detector, said detector carrying a sample port for receiving said gas sample and an exhaust port for expelling said gas sample;
passing said at least two different reporters carried by said portion of said substrate into said sample area wherein said sample area precludes exposure of said at least two different reporters outside of said sample area to said gas sample;
communicating said gas sample to said at least two different reporters positioned within said sample area within said detector;
heating said substrate positioned within said sample area and said gas sample entering said sample area;
causing a response between at least one analyte and said at least two different reporters, said at least one analyte carried by said gas sample;
detecting said response with said optical detector, said detecting step identifying said at least one analyte;
notifying said control system regarding the identity of said at least one analyte; and
communicating said notifying step to a display, said communicating being controlled by said control system.

27. The method of claim 26, further comprising advancing said substrate through said isolated sample area.

28. An apparatus for detecting an analyte substance in a gas sample comprising:
a flow system carrying a sensor head and a heating block, said sensor head and said heating block defining a module receiver therebetween;
a gas inlet positioned on said sensor head and providing gaseous fluid communication to a sample area;
a gas outlet positioned on said sensor head and providing gaseous fluid communication from said sample area;
a sealing edge positioned on the bottom of said sensor head and within said module receiver;
a removable module positioned in said module receiver and carrying a substrate and a substrate feeder capable of advancing said substrate through said module, said module carrying a window;
said substrate carrying at least two different reporters thereon, wherein said two different reporters are selected for their ability to respond to at least one analyte carried by said gas sample, wherein said substrate is exposed to said gas sample in said sample area and said sample area is located within said window, wherein said sample area is defined by said bottom of said sensor head, said sealing edge, and said substrate, wherein said sealing edge and said substrate define a leak-free seal therebetween, wherein said sample area isolates a portion of said substrate carrying said at least two different reporters thereon from a remainder of said substrate located outside said sample area, and wherein said sample area precludes contamination of said remainder of said substrate located outside of said sample area;

at least one optical port in optical communication with said sample area, said optical port providing optical communication for at least one optical illuminator and for at least one optical detector communicating therethrough.

29. The apparatus of claim 28, further comprising a contaminate binder positioned near said gas inlet.

30. The apparatus of claim 28, wherein said removable module is a reel-to-reel cartridge, and wherein said substrate comprises a flexible substrate.

31. The apparatus of claim 28, wherein said removable module is a strip feed cartridge.

32. The apparatus of claim 28, wherein said removable module is a rotating disk cartridge.

33. The apparatus of claim 28, wherein said substrate feeder is capable of automatically advancing said substrate in said removable module through said window, thereby exposing said substrate to said sample area.

34. The apparatus of claim 28, further comprising a heater positioned within said module receiver and positioned to provide heat specifically to said module receiver, said gas inlet, and/or a sample port of said apparatus.

35. The apparatus of claim 28 further comprising a control system in electronic communication with said optical illuminator, said optical detector, and said removable module, said control system comprising a processor and a memory device.

* * * * *